United States Patent
Bartos et al.

(10) Patent No.: US 8,841,350 B2
(45) Date of Patent: Sep. 23, 2014

(54) METHOD FOR INDUCING UDP-GLUCURONOSYLTRANSFERASE ACTIVITY USING PTEROSTILBENE

(75) Inventors: Jeremy Bartos, Orange, CA (US); Ryan Dellinger, Irvine, CA (US)

(73) Assignees: ChromaDex Inc., Irvine, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/466,827

(22) Filed: May 8, 2012

(65) Prior Publication Data

US 2012/0289605 A1    Nov. 15, 2012

Related U.S. Application Data

(60) Provisional application No. 61/484,977, filed on May 11, 2011.

(51) Int. Cl.
*A61K 31/09* (2006.01)

(52) U.S. Cl.
USPC .......... 514/720; 514/733

(58) Field of Classification Search
CPC ............. A61K 31/05; A61K 31/09
USPC .................. 514/733, 720
See application file for complete search history.

(56) References Cited

U.S. PATENT DOCUMENTS

| | | | |
|---|---|---|---|
| 6,414,037 B1 * | 7/2002 | Pezzuto et al. | 514/733 |
| 6,955,804 B2 * | 10/2005 | Brown et al. | 424/59 |
| 2008/0213198 A1 | 9/2008 | Lintner et al. | |
| 2009/0118622 A1 | 5/2009 | Durkin et al. | |
| 2009/0175803 A1 * | 7/2009 | Rubin et al. | 424/48 |
| 2009/0324740 A1 | 12/2009 | Albritton, IV | |
| 2011/0136751 A1 | 6/2011 | Estrela et al. | |
| 2011/0224290 A1 | 9/2011 | Estrela Ariquel et al. | |

FOREIGN PATENT DOCUMENTS

| | | |
|---|---|---|
| WO | 03/049713 A1 | 6/2003 |
| WO | 2011051483 A1 | 5/2011 |

OTHER PUBLICATIONS

Schneider et al. The American Journal of Surgery, 2009, vol. 198, pp. 679-684.*
Lucie Fremont, Life Sciences, vol. 66, No. 8, pp. 663-673, 2000.*
Sabolovic et al. Biopharm. Drug Dispos. 27: 181-189 (2006).*
Kapetanovic, I.M., et al., Pharmacokinetics, oral bioavailability, and metabolic profile of resveratrol and its dimethylether analog, pterostilbene, in rats, Cancer Chemother.Pharmacol. (2010) publ. online Nov. 30; DOI 10.1007/s00280-010-1525-4 (Berlin:Springer-Verlag Publ.).
Mikstacka, R., et al., Inhibition of human recombinant cytochromes P450 CYP1A1 and CYP1B1 by trans-resveratrol methyl ethers, Mol. Nutr. Food Res. (2007) 51:517-524.

(Continued)

*Primary Examiner* — Savitha Rao
*Assistant Examiner* — Angela Brown-Pettigrew
(74) *Attorney, Agent, or Firm* — Amin Talati, LLC; George M. Carrera, Jr.; Jonathan J. Krit (57) ABSTRACT

A method is provided for treating an individual for a cellular proliferative disorder, including administering to the individual in need of such treatment a therapeutically effective amount of the compound pterostilbene wherein UDP-glucuronosyltransferase (UGT) activity is increased. In an embodiment, 12-HETE levels can be reduced by administration of pterostilbene.

18 Claims, 6 Drawing Sheets

(56) References Cited

OTHER PUBLICATIONS

Barbier, O., et al., Peroxisome Proliferator-activated Receptor Alpha Induces Hepatic Expression of the Human Bile Acid Glucuronidating UDP-glucuronosyltransferase 2B4 Enzyme, J. Biol. Chem. (2003) 278(35):32852-32860.

Barbier, O., et al., the UDP-glucuronosyltransferase 1A9 Enzyme Is a Peroxisome Proliferator-activated Receptor Alpha and Gamma Target Gene, J. Biol. Chem. (2003) 278(16):13975-13983.

Bing-Rong, Z., et al., Protective effect of the Baicalin against DNA damage induced by ultraviolet B irradiation to mouse epidermis, Photoderm., Photoimmunol. & Photomed. (2008) 24:175-182.

Boehnke, K., et al., Stem cells of the human epidermis and their niche: Composition and function in epidermal regeneration and carcinogenesis, Carcinogenesis (2012) published online Mar. 29; Abstract Only.

Chen, G., et al., Identification of a prevalent functional missense polymorphism in the UGT2B10 gene and its association with UGT2B10 inactivation against tobacco-specific nitrosamines, Pharmacogenetics and Genomics (2008) 18(3):181-191; Abstract Only.

Chow, H-H., et al., Resveratrol Modulates Drug- and Carcinogen-Metabolizing Enzymes in a Healthy Volunteer Study, Cancer Prev. Res. (2010) 3(9):1168-1175.

Cichocki, M., et al., Pterostilbene is equally potent as resveratrol in inhibiting 12-O-tetradecanoylphorbol-13-acetate activated $NF_KB$, AP-1, COX-2, and iNOS in mouse epidermis, Molecular Nutr. & Food Res. (2008) 52 (Suppl. 1):S62-S70; Abstract Only.

Dellinger, R., et al., Glucuronidation of PhIP and N-OH-PhIP by UDP-glucuronosyltransferase 1A10, Carcinogenesis (2007) 28(11):2412-2418.

De Luca, M., et al., Human Epithelial Cells Induce Human Melanocyte Growth In Vitro but Only Skin Keratinocytes Regulate Its Proper Differentiation in the Absence of Dermis, J. Cell Biol. (1988) 107:1919-1926.

Ferrer, P., et al., Nitric Oxide Mediates Natural Polyphenol-induced Bcl-2 Down-regulation and Activation of Cell Death in Metastatic B16 Melanoma, J. Biol. Chem. (2007) 282(5):2880-2890.

Ferrer, P., et al., Association between Pterostilbene and Quercetin Inhibits Metastatic Activity of B16 Melanoma, Neoplasia (2005) 7(1):37-47.

Hougee, S., et al., Selective COX-2 Inhibition by a Pterocarpus marsupium Extract Characterized by Pterostilbene, and its Activity in Healthy Human Volunteers, Planta Med. 71(5):387-392; Abstract Only, (2005).

Jang, M., et al., Cancer Chemopreventive Activity of Resveratrol, a Natural Product Derived from Grapes, Science (1997) 275:218-220.

Jiang, Y.J., et al., LXR and PPAR activators stimulate cholesterol sulfotransferase type 2 isoform 1b in human keratinocytes, J. Lipid Res. (2005) 46:2657-2666.

Krieg, P., et al., 12-Lipoxygenase isoenzymes in mouse skin tumor development, Molecular Carcinogenesis (1995) 14(2):118-129; Abstract Only.

Nichols, Jr., S.E., et al., The Occurrence and Morphogenesis of Melanocytes in the Connective Tissues of the PET/MCV Mouse Strain, J. Embryol. Exp. Morphol. (1960) 8:24-32.

Rimando, A.M., et al., Pterostilbene, a New Agonist for the Peroxisome Proliferator-Activated Receptor r-Isoform, Lowers Plasma Lipoproteins and Cholesterol in Hypercholesterolemic Hamsters, J. Agric. Food Chem. (2005) 53:3403-3407.

Rimando, A.M., et al., Cancer Chemopreventive and Antioxidant Activities of Pterostilbene, a Naturally Occurring Analogue of Resveratrol, J. Agric. Food Chem. (2002) 50:3453-3457.

Runge-Morris, M., et al., Regulation of Sulfotransferase and UDP-Glucuronosyltransferase Gene Expression by the PPARs, PPAR Res. (2009), Article ID 728941, pp. 1-14 (New York: Hindawi Publ. Corp.).

Schneider, J.G., et al., Effects of pterostilbene on melanoma alone and in synergy with inositol hexaphosphate, Am. J. Surg. (2009) 198:679-684.

Senekeo-Effenberger, K., et al., Expression of the Human UGT1 Locus in Transgenic Mice by 4-Chloro-6-(2,3-xylidino)-2-pyrimidinylthioacetic Acid (WY-14643) and Implications on Drug Metabolism through Peroxisome Proliferator-Activated Receptor Alpha Activation, Drug Metab. Disposition (2007) 35(3):419-427.

Shleby, M.K., et al., Induction of Rat UDP-Glucuronosyltransferases in Liver and Duodenum by Microsomal Enzyme Inducers That Activate Various Transcriptional Pathways, Drug Metab. Disposition (2006) 34(10):1772-1778.

Turgeon, D., et al., Glucuronidation of arachidonic and linoleic acid metabolites by human UDP-glucuronosyltransferases, J. Lipid Res. (2003) 44:1182-1191.

Virmani, J., et al., Role of 'platelet-type' 12-lipoxygenase in skin carcinogenesis, Cancer Lett. (2001) 162:161-165.

\* cited by examiner

METHOD FOR INDUCING UDP-GLUCURONOSYLTRANSFERASE ACTIVITY USING PTEROSTILBENE

This application claims the benefit of earlier filed U.S. Provisional application No. 61/484,977, filed on May 11, 2011, which is hereby incorporated by reference herein.

FIELD OF THE INVENTION

A process for increasing or inducing UDP-glucuronosyltransferase (UGT) activity using an effective amount of pterostilbene is described in connection with methods of treatment for cellular proliferative disorders. Pharmaceutical and nutraceutical formulations containing pterostilbene suitable for administration to an individual for inducing UDP-glucuronosyltransferase (UGT) activity are described.

BACKGROUND

During Phase II metabolism, an endogenous or exogenous substrate is rendered more hydrophilic through the covalent attachment of an endogenous molecule. Phase II is also referred to as conjugative metabolism, since conjugating moieties such as sulfonates, glucuronates, glutathiones, glycinates, acetates, and methylates, can be formed. Usually, Phase II metabolism is used by the body to increase the hydrophilicity of the substrate molecule, which facilitates transport and elimination of the conjugate product.

Phase II glucuronidation reactions are catalyzed by the UDP-glucuronosyltransferase (UGT) family of enzymes. The glucuronidation reaction consists of the transfer of the glucuronosyl group from uridine 5'-diphospho-glucuronic acid (UDP-GA) to substrate molecules that contain oxygen, nitrogen, sulfur or carboxyl functional groups. UGT enzymes represent a highly responsive defense system against the mutagenicity of carcinogens and the toxicity of both xenobiotics and endogenous metabolic intermediates. Also, in metabolically active tissues, certain transcription factors, such as the peroxisome proliferator-activated receptors (PPARs) play an active role in the regulation of UGT gene expression and activity. See, Runge-Morris, et al, *PPAR Res.* (2009), Article ID 728941, 14 pages, "Regulation of Sulfotransferase and UDP-Glucuronosyltransferase Gene Expression by the PPARs" (Hindawi Publ. Co., New York).

Glucuronidation plays a physiological role in the modulation of biologically active endogenous hormones and metabolic intermediates. One important endogenous UGT substrate is bilirubin, the metabolism of which is tightly controlled by UGT1A1, thus forming the elimination product bilirubin diglucuronide. Another isoform, UGT2B4, is known to be the major bile acid conjugating UGT enzyme in human liver, catalyzing glucuronidation of hyodeoxycholic acid. Further, it has been observed that various isoforms of UGTs are inducible, and the regulation of their activity may be an important determinant of drug detoxification and elimination. For example, PPARs serve an important role in the regulation of UGTs (Barbier, et al., *J. Biol. Chem.* (2003) 278:32852-32860).

The PPAR nuclear receptor network represents a central determinant of cellular energy balance. In heterodimeric partnership with the retinoid X receptor (RXR), PPAR forms a ligand-activated nuclear receptor transcription factor that is capable of integrating the expression of a wide spectrum of target genes (including UGTs) involved in cellular lipid metabolism, energy homeostasis, and inflammation. PPAR-alpha isoform expression is most prominent in the liver, kidney, and heart where it is engaged in the regulation of fatty acid oxidation. PPAR-alpha can also mediate induction of biotransformation enzymes. Using the key-lock analogy for enzyme receptor activation binding, fatty acids represent a major source of cellular energy and are important physiological activators of PPAR-alpha. The aforementioned PPAR-RXR heterodimer, in association with other co-activators, binds to DNA sequences called peroxisome proliferator response elements (PPREs) in the regulatory region of a target gene, initiating transcription and translation of enzymes, such as UGTs, and the like.

Therefore, in order to regulate the expression and activation of UGTs, one must provide an appropriate and selective enzyme inducer. Certain UGT inducers in humans are known, such as clofibrate, which is a PPAR-alpha agonist (Barbier, loc. cit.). In rats, UGT1A1 is a PPAR-alpha target gene, and exposure to certain inducers such as PPAR-alpha agonists can increase mRNA expression of this UGT in the liver (Shelby, et al., *Drug Metab. and Disposition* (2006) 34:1772-1778).

Furthermore, the UGTs have been shown to glucuronidate and inactivate 12-hydroxyeicosatetraenoic acid, or 12(S)-HETE ("12-HETE"). See, Turgeon, et al. *J. Lipid Res.* (2003) 44:1182-1191. As a response to certain inflammatory processes, and also UV-induced damage and/or skin carcinogenesis, arachidonic acid ("AA"), a fatty acid naturally present in membrane phospholipids, is metabolized by lipoxygenases (LOX) to a number of active eicosanoids. LOX metabolism of AA leads to the production of leukotrienes and hydroxyeicosatetraenoic acids (HETE). 5-LOX is responsible for the production of leukotrienes and 5-HETE, while 12-LOX yields 12-HETE. Specifically, lipoxygenase converts AA to the unstable hydroperoxy-eicosatetraenoic acid (HPETE), which is then hydrolyzed by peroxidase into HETE. Mounting evidence has shown that both 5-LOX and 12-LOX metabolites promote carcinogenesis through resistance to apoptosis as well as increased proliferation, angiogenesis and cell migration. Both 5-LOX and 12-LOX, which are largely absent from normal epithelia, are often constitutively expressed in various epithelial cancers.

Elevated levels of 12-LOX mRNA has also been linked to late stage cancer and poor prognosis. Additionally, 12-LOX has been demonstrated to play a direct role in skin carcinogenesis in mouse models, and 12-HETE has been detected at elevated levels in skin tumors compared to normal skin in mice. Specifically, levels of 12-HETE were 50-fold higher in papillomas and squamous cell carcinomas than in normal skin from the same mouse (Virmani, J., et al., *Cancer Lett.* (2001) 162(2): 161-165; Krieg, P., et al., *Mol. Carcinog.* (1995) 14(2): 118-129). Another mouse model demonstrated that use of a specific 12-LOX inhibitor (Baicalin) was protective against UVB-induced DNA damage in the skin (Bing-Rong, Z., et al., *Photodermatol. Photoimmunol. Photomed.* (2008) 24(4): 175-182). This result further underscores the importance of 12-HETE in skin cancer progression. Thus, without intending to be bound by theory, it is hypothesized that human skin cancer may be treated or prevented through inhibition of 12-LOX directly, or by inhibition of 12-LOX signaling, namely, by reduction in the 12-HETE levels. As discussed above, UGTs can glucuronidate, and thus inactivate 12-HETE, leading to its elimination by the body. However, UGTs expressed in the skin can be down-regulated by UV radiation, which is a prime suspect causative agent in skin cancers and other proliferative disorders.

In view of the above, it would be desirable to provide an enzyme inducer or agonist that can activate or induce expression of UGTs by administration of said inducer to an individual, animal or human. Further, it is expected that an enzyme inducer or agonist that can activate or induce expression of UGTs would also reduce levels of 12-HETE, which would serve as a useful contribution to the art.

In addition, use of an enzyme inducer or agonist for treatment of an individual for a cellular proliferative disorder, including skin cancer, comprising administering to the individual in need of such treatment a therapeutically effective amount of the compound pterostilbene wherein UDP-glucuronosyltransferase (UGT) activity is increased, would represent a useful contribution to the art.

SUMMARY OF THE INVENTION

A method of treating an individual for a cellular proliferative disorder is provided, comprising administering to the individual in need of such treatment a therapeutically effective amount of the compound pterostilbene wherein UDP-glucuronosyltransferase (UGT) activity is increased.

In an alternative embodiment, a method of preventing or inhibiting the UV-induced loss of UDP-glucuronosyltransferase (UGT) activity in an individual (e.g., an individual afflicted with a cellular proliferative disorder) is provided, comprising administering to the individual in need of such treatment a therapeutically effective amount of the compound pterostilbene wherein UDP-glucuronosyltransferase (UGT) activity is increased.

In a further embodiment, 12-HETE levels in pre-cancerous actinic keratoses (AK) lesions can be reduced by administration of pterostilbene.

In a yet further embodiment, 12-LOX expression levels in pre-cancerous, proliferating cells, or malignant cells, may be reduced by administration of pterostilbene.

DETAILED DESCRIPTION

A safe and effective dietary supplement has been provided containing pterostilbene, which can be administered in a therapeutically effective amount to an individual for treatment of a cellular proliferative disorder. In one embodiment, a method of treating an individual for a cellular proliferative disorder comprises the step of administering to the individual in need of such treatment a therapeutically effective amount of the compound pterostilbene wherein UDP-glucuronosyltransferase (UGT) activity is increased.

In an embodiment, said safe and effective dietary supplement containing pterostilbene will cause regression of actinic keratoses (AKs) and other precancerous changes associated with UV-induced photodamage of the skin. Furthermore, said dietary supplement containing pterostilbene will be used for the treatment, suppression and/or prevention of non-melanoma skin cancers (NMSCs).

In a further embodiment, a method of inhibiting the loss of UDP-glucuronosyltransferase (UGT) activity an individual afflicted with a cellular proliferative disorder comprises the step of administering to the individual in need of such treatment a therapeutically effective amount of the compound pterostilbene wherein UDP-glucuronosyltransferase (UGT) activity is increased.

The UDP-glucuronosyltransferases (UGTs) catalyze the transfer of glucuronic acid from a high-energy cofactor, UDP-glucuronic acid, to a xenobiotic, drug, or endogenous substrate containing an available reactive or nucleophilic center such as a hydroxyl, carboxyl, amino, or thiol group. The UGTs are Phase II biotransformation enzymes predominantly expressed in liver and intestine, and are membrane-bound enzymes localized on the luminal surface of the endoplasmic reticulum. Relative to the parent substrate, the end-products of glucuronidation are typically more polar and better suited for excretion and elimination through the urine or bile.

Endogenous UGT substrates include bilirubin, neutral steroids, bile acids, fatty acids, and retinoids. Xenobiotic UGT substrates range from environmental toxicants such as benzo [a]pyrene to common pharmaceuticals such as acetaminophen and other NSAIDs. Individual UGT isoforms display distinctive patterns of substrate specificity and inducible regulation. Different UGTs are expressed in a species- and tissue-specific manner. The two major UGT gene families are UGT1 and UGT2.

PPARs are known to be involved in the regulation of UGTs. In particular, the UGTs are targets of PPAR-alpha, as opposed to PPAR-gamma. Resveratrol, a known PPAR-gamma activator, has shown some induction of UGTs, but is not an activator of PPAR-alpha. In one study of a group of similar stilbenes, only pterostilbene activated PPAR-alpha, in a manner similar to ciprofibrate (Rimando, et al., *J Agric. Food Chem.* (2005) 53:3403-3407). Pterostilbene is not thought to be an activator of PPAR-gamma. This sub-type selectivity is thought to be advantageous in the present approach to activate or induce expression of UGTs using pterostilbene.

UGTs have been shown to glucuronidate and inactivate 12-hydroxyeicosatetraenoic acid (12-HETE), which is produced by the enzyme 12-LOX during the process of UV-induced skin carcinogenesis, for example. It has been discovered that pterostilbene, and nutraceutical formulations thereof, can induce UGT activity, thus reducing 12-HETE levels in the skin.

Figure 1:
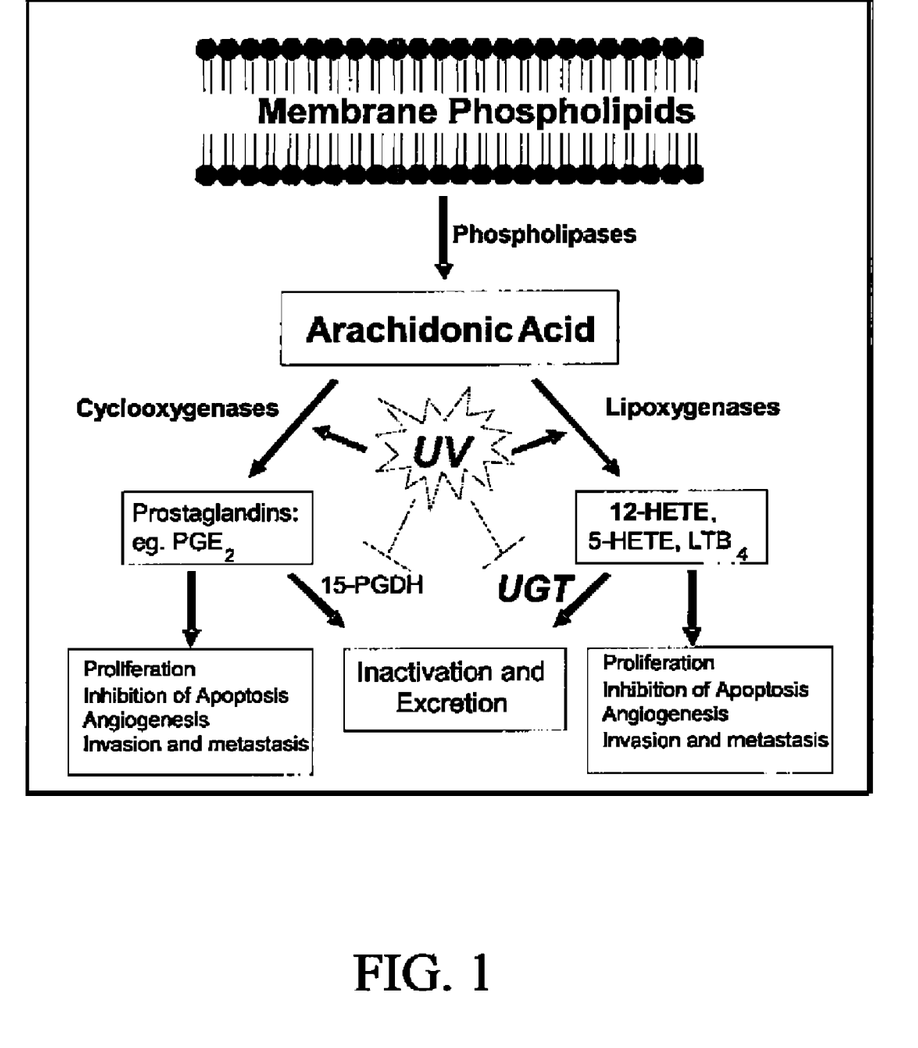
FIG. 1 describes a proposed metabolic pathway in an embodiment of the present invention, in which UGTs can inactivate 12-HETE.

FIG. 1 shows a model of arachidonic acid (AA) metabolism and UGT conjugative metabolism. Cyclooxygenses can also play a role in inflammatory processes, but are not discussed herein. Overall, FIG. 1 shows the proposed role of AA metabolism in UV-induced skin cancer progression (or other types of UV-induced skin damage, e.g., sunburn), including production and metabolism of 12-HETE.

Non-melanoma skin cancer (NMSC) is by far the most common cancer that plagues man. The incidence of NMSC is nearly as great as all other forms of cancer combined. For 2007, the American Cancer Society estimated that more than one million new cases of non-melanoma skin cancers were diagnosed in the United States, and that there were approximately 2,700 deaths related to non-melanoma skin cancer. However, these estimates are low given that squamous cell carcinoma and basal cell carcinoma of the skin are not required to be reported and, thus, the number of actual cases annually is probably over three million. There are two primary types of NMSC: basal cell carcinoma accounts for approximately 80% of the cases, while squamous cell carcinoma accounts for approximately 20%. The majority of deaths from NMSC are caused by squamous cell carcinoma. Most NMSC, including squamous cell carcinoma, are caused by sun exposure with resultant photocarcinogenesis. Treatment for NMSC is surgical, often resulting in scarring and other morbidities.

Actinic keratoses (AKs) are precancerous cutaneous neoplasms, which can give rise to squamous cell carcinoma. They arise as a result of long-term sun exposure. Other causes of AKs and NMSC are UV light from tanning booths or arc welding, x-irradiation, or exposure to certain chemicals. AKs are extremely common lesions and are present in more than 10 million Americans. The yearly rate of progression of an AK in an average-risk person in Australia is between 8 and 24 per 10,000. High-risk individuals (those with multiple AKs) have progression rates as high as 12-30 percent over 3 years. Two percent of squamous cell cancers originating in AKs may metastasize, and 7 percent recur locally. Actinic keratoses are treated most commonly with liquid nitrogen or a topical chemotherapeutic, such as, for example, 5-fluorouracil. Less commonly they are treated with other topical agents (diclofenac and imiquimod), photodynamic therapy, chemical peels or non-fractionated or fractionated ablative laser resurfacing.

In the instant specification, it will be understood that "actinic keratosis" is the proliferative disorder that produces AKs.

While some treatments are known, it would be desirable to proactively prevent or inhibit formation of actinic keratosis and skin cancers in order to reduce treatment costs, morbidity, and mortality. A lifetime of sun protection is an excellent method for minimizing risk of development of actinic keratosis and non-melanoma skin cancers. However, a large percentage of patients already have extensive photodamage and changing sun-protective behaviors has proven to be difficult.

An ideal chemopreventive agent could achieve regression of precancerous changes, prevent development of NMSC and minimize ultraviolet light associated damage with minimal or no side effects. As noted above, there are topical agents that can remove actinic keratoses but they generally result in significant inflammation at the treatment site. A novel approach is required.

Human skin comprises a top epidermal layer (epidermis) which rests on a lower dermal layer (dermis). The epidermis is made up primarily of keratinocytes, which develop at the bottom, move toward the top, and are constantly replaced. As old dead cells are shed, they are replaced, so this layer is constantly renewing itself. The epidermis also contains melanocytes, located generally near the bottom of the layer, which produce the pigment melanin, contributing to skin color, and also providing UV-protection. The epidermis also contains dendritic (Langerhans) cells, which are involved in the immune system, and basal cells found at the bottom of the layer. The epidermis also includes squamous cells. The epidermal and dermal layers also contain stem cells and hair follicles. In mammals, melanocytes are also distributed in the brain, eye, ear, and heart, among other tissues.

The skin cells as described are susceptible to UV light-induced damage, DNA damage, and carcinogenesis.

Pterostilbene (3,5-dimethoxy-4'-hydroxy-trans-stilbene) is an orally bioavailable compound with a half life $t_{1/2}$ of about 105 minutes in blood. In contrast, resveratrol has poor bioavailability, and is readily metabolized by UGTs leading to a much shorter half life ($t_{1/2}$ about 14 minutes in blood), which hinders its effectiveness as a chemopreventive agent.

Several studies have shown that resveratrol prevents UV-B mediated cell damage in mouse skin when given orally or applied topically (Afaq, F., et al., "Prevention of short-term ultraviolet B radiation-mediated damages by resveratrol in SKH-1 hairless mice," *Toxicol. AppL Pharmacol.* (2003) 186 (1): 28-37; Reagan-Shaw, S., et al., "Modulations of critical cell cycle regulatory events during chemoprevention of ultraviolet B-mediated responses by resveratrol in SKH-1 hairless mouse skin," *Oncogene* (2004) 23(30): 5151-60; and Aziz, M. H., et al., "Prevention of ultraviolet-B radiation damage by resveratrol in mouse skin is mediated via modulation in survivin," *Photochem. Photobiol.* (2005) 81(1): 25-31). Resveratrol has also been shown to induce UGT activity (Chow, H. H., et al., "Resveratrol modulates drug- and carcinogen-metabolizing enzymes in a healthy volunteer study," *Cancer Prev. Res.* (Phila. Pa.), (2010) 3(9): 1168-75). However, its use in humans as a chemopreventative agent seems to be unlikely (at least as a single agent) due to poor bioavailability. Resveratrol is well tolerated in humans, but is readily metabolized (by the UGTs ironically) leading to a short half-life which hinders its effectiveness as a chemopreventative agent.

Pterostilbene is found in grapes and berries. It is a naturally occurring dimethylated analog of resveratrol, but has a longer half-life most likely due to the methyl groups which may dramatically reduce its metabolism by UGTs (Hougee, S., et al., "Selective COX-2 inhibition by a Pterocarpus marsupium extract characterized by pterostilbene, and its activity in healthy human volunteers," *Planta Med.* (2005) 71(5): 387-92). Pterostilbene has been shown to be equally or significantly more potent than resveratrol in several biological assays in mice including inhibition of NF-KB, AP-1 and iNOS activation in mouse skin (Cichocki, M., et al., "Pterostilbene is equally potent as resveratrol in inhibiting 12-O-tetradecanoylphorbol-13-acetate activated NFkappaB, AP-1, COX-2, and iNOS in mouse epidermis," Mol. Nutr. Food Res. (2008) 52 Suppl 1: S62-70).

It is believed that a nutraceutical formulation comprising pterostilbene or a derivative thereof can be used to advantageously increase the activity of, or induce the in vivo expression of UDP-glucuronosyltransferases (UGTs). This up-regulation of UGTs can inhibit or prevent the loss of UGTs caused by certain factors, including down-regulation in response to UV radiation observed in human keratinocytes or melanocytes, for example. See FIG. 1.

Useful therapeutic dosages of pterostilbene can range, but are not limited to, from about 5 mg to about 1000 mg in a human individual. Another suitable dose range is from about 20 mg to about 250 mg. Pterostilbene may be formulated as a pharmaceutical or nutraceutical composition, including a pharmaceutically or nutraceutically acceptable carrier, respectively. In one embodiment of a pharmaceutical composition containing pterostilbene, a suitable level of pterostilbene may range from about 0.1% by weight to about 10% by weight, based on the total weight of the composition.

The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use an oil-base is preferred.

The pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

Pterostilbene can be provided in daily dosages of from about 50 mg to about 250 mg, in a human patient, for example. Another suitable dosage range is from about 50 mg to about 150 mg daily. Another suitable dosage range is from about 50 mg to about 100 mg daily. A particularly suitable dosage is about 100 mg administered daily.

When skin is used as a target organ, levels of 12-HETE in AK lesions can be determined to assess induction of expression of UGTs in an individual both prior to and after receiving pterostilbene supplementation. The following is a general study design for a Phase II clinical trial to assess efficacy of pterostilbene to induce expression and/or increase activity of UGTs, and to decrease levels of 12-HETE and/or inhibit expression of 12-LOX, amongst other measurable endpoints.

Study Population

Thirty-four to forty subjects with a history of squamous cell carcinoma and who have current actinic keratoses will complete the trial. Individuals at high risk for NMSC are tested, and are greater than 18 years of age. Specifically, subjects will have had at least one squamous cell carcinoma within the last 5 years and now have at least 10 actinic keratoses (AKs) on their forearms.

Study Design

The study provides the opportunity to evaluate a novel method for suppression or prevention of NMSC. It utilizes a variety of endpoints from analysis of molecular markers to standard clinical assessment to state of the art compositional imaging. This design allows for an economy of effort, testing the putative agent first clinically, with associated key endpoint biomarkers for which valuable validation data can be obtained.

Eligible subjects can receive pterostilbene orally at a dose in a range of about 50 mg to about 250 mg. In one embodiment a patient will receive 100 mg of pterostilbene orally, on a daily basis. Pterostilbene can be provided in an appropriate nutraceutical formulation in combination with, or co-administered with, a nutraceutically acceptable carrier. Alternatively, pterostilbene can be provided in an appropriate pharmaceutical formulation in combination with, or co-administered with, a pharmaceutically acceptable carrier.

Duration of therapy can be up to about 12 weeks. Subjects will be evaluated at 4, 8 and 12 weeks of the study therapy, and then post-treatment, at weeks 16 and 20 of the study.

Imaging of AK lesions can be carried out using wide-field functional imaging (WiFI) technology to measure changes in blood flow, fat and water content, for example, prior to and after pterostilbene supplementation. Wide-field Functional Imaging (WiFI) is the integration of two wide-field imaging modalities: spatially modulated reflectance/fluorescence imaging (MI) and laser speckle imaging (LSI). WiFI can simultaneously measure tissue blood flow and biochemical composition (i.e. oxy- and deoxy-hemoglobin, water and lipid content) in turbid tissues. It possesses sufficient spatio-temporal resolution to study both fast (i.e., milliseconds timescale) and localized (i.e., tens of µm to mm) events at depths of several millimeters in thick tissues. Subjects will have these safe (similar to standard digital photography, but done using red and near infrared light being placed on the skin), quick (10 minutes or less) non-invasive measurements performed at each visit. These tests are available at the Beckman Laser Center at University of California, Irvine. WiFI of 8 $cm^2$ section of sun damaged skin containing at least 3 AKs will be performed at each clinic visit. We anticipate observing decreased blood flow in AK at 12 weeks compared to pre-treatment.

Thus, blood flow will be examined by non-invasive WiFI imaging as well as fat and water content of mapped AK. Since 12-HETE is capable of stimulating angiogenesis through activation of vascular endothelial growth factor (VEGF), we anticipate observing decreased blood flow to the AK lesion after pterostilbene supplementation Study Schedule An initial screening visit is to be performed for each patient, including, but not limited to, a dermatology review, i.e. complete skin exam of arms, limbs, and other skin areas for AKs and/or sun damage. The following tests can also be run: blood testing (CBC with differential), comprehensive metabolic panel, lipid panel, and urinalysis.

Within 4 weeks of the screening visit, lab and blood tests are reviewed. Photographs and counting of AKs on bilateral forearms are made. An area of study is then chosen on the skin of the patient (8 cm×8 cm), and is designated and mapped on a transparency. The mapped areas chosen will have at least three AKs and may be either right or left arm. Designation of pre- and post-biopsy areas are made, as well as imaging sites. Biopsy specimens of suspected NMSCs are collected. Non-invasive imaging (i.e. WiFI) can be performed at this stage.

In one embodiment, a skin biopsy site can be designated as pre-treatment AK (pre-AK). If biopsy results reveal no AK but atypical cell structures, the subject may continue treatment and be monitored.

Through the later time periods of the clinical study, for example at 4, 8 and 12 weeks, the skin study area is monitored and examined, photographed and/or imaged. Patients will be monitored for adverse events.

At the end of 12 weeks, the skin study area will be examined, photographed, and imaged. Specifically, AKs on bilateral forearm(s) of each patient are photographed and counted. Post-treatment biopsy specimens of suspected NMSCs and post-treatment AK sites (post-AK) are then collected and analyzed, along with blood and urine testing as above.

In an embodiment, at 16 and 20 weeks post-treatment (or at some other scheduled time point before or after), the skin study area will be mapped, examined, photographed, and imaged, as above.

Tissue Samples and Biomarker Evaluation 4 mm AK biopsy at start (pre treatment) and post treatment (12 weeks) are obtained from each patient. Biopsies will be cut in half. Immediately following the clinical biopsy procedure, the sample will be sliced and one half will be sent for histopathologic analysis, while the remainder of the sample will be sent to the laboratory for biomarker analysis. All biomarker analysis will be performed in batches of 4 patients after completion of treatment so paired samples may be analyzed together.

Arachidonic acid metabolite (12-HETE and $PGE_2$) levels (pg/mg protein) will be determined from actinic kerotoses pre-treatment and then compared to post treatment levels using liquid chromatography coupled to a triple quad mass spectrometer (LC/MS/MS) following established protocols. Assay requires tissue extraction, sonication, centrifugation and protein content determination to prepare samples followed by LC/MS/MS. It is expected that levels of 12-HETE and $PGE_2$ in AK will be significantly reduced after pterostilbene treatment or pterostilbene supplementation.

Protein levels of COX-2, 12-LOX, UGT and 15-PGDH will be measured semi-quantitatively by Western blot normalized to actin following established protocols. Changes in expression levels from AK following pterostilbene treatment will be compared to pre-treatment levels and reported as fold changes following densitometry. It is expected that COX-2 and 12-LOX expression will be significantly reduced after pterostilbene treatment. Conversely, it is expected that UGT and 15-PGDH protein levels will be significantly increased in AK following pterostilbene supplementation.

Clinical Trial Endpoints

Above study describes a single arm trial with no randomization and no control group. The primary objective of the study is to evaluate levels of the bioactive lipid 12-hydroxyeicostetraenoic acid (12-HETE) in precancerous actinic keratoses (AK) lesions from subjects prior to and after receiving pterostilbene supplementation. Without intending to be bound by theory, the hypothesis is that the study therapy will prove to be a safe and effective nutraceutical that will cause regression of precancerous actinic keratoses and reverse other precancerous changes associated with photo-damage of the skin. Subjects who demonstrate ≥80% compliance with all doses of the assigned study agent will be considered evaluable for the primary endpoint, 12-HETE (pg/mg protein). Secondary endpoints include $PGE_2$ (pg/mg protein) and enzyme protein levels of UGT, COX-2, 15-PDGH, and 12-LOX. Additional secondary endpoints include blood flow, fat and water content measured in AK lesions, number of original AK lesions, number of new AK lesions, and number of non-melanoma skin cancers (NMSCs).

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, pterostilbene may be combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

Routes of Administration

The compounds may be administered by any route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of pterostilbene in the body of the patient in a controlled formulation, with systemic or local release of the drug to occur at a later time. For example, the drug may be localized in a depot for controlled release to the circulation, or for release to a local site of tumor growth.

The treatment may be carried out for as long a period as necessary, either in a single, uninterrupted session, or in discrete sessions. The treating physician will know how to increase, decrease, or interrupt treatment based on patient response. According to one embodiment, treatment is carried out for from about four to about twelve weeks. The treatment schedule may be repeated as required.

Pterostilbene, and nutraceutical formulations thereof, is believed to be effective against a range of cancers and tumor types, including skin cancers, including, but not limited to basal cell carcinoma, squamous cell carcinoma, malignant melanoma, Kaposi's sarcoma, Merkel cell carcinoma, cutaneous lymphoma, moles, dysplastic nevi, lipoma, angioma, dermatofibroma, keloids, and psoriasis.

Skins cancers may be solid tumors that may or may not be metastatic. Thus, the term "tumor cell", as provided herein, includes a cell afflicted by any one of the above identified disorders.

Other cellular proliferative disorders are susceptible to treatment by the pterostilbene formulations described herein, including, but not limited to, cancers selected from the group consisting of breast cancer, ovarian cancer, cervical cancer, prostate cancer, testicular cancer, colorectal cancer, lung cancer, renal cancer, liver cancer, brain cancer, stomach cancer, bronchial cancer, pancreatic cancer, bladder cancer, and bone cancer.

Pterostilbene, and nutraceutical formulations thereof, is also believed to be useful in the treatment of non-cancer cellular proliferative disorders, that is cellular proliferative disorders which are characterized by benign indications. Such disorders may also be known as cytoproliferative or hyperproliferative in that cells are made by the body at an atypically elevated rate. Non-cancer cellular proliferative disorders believed treatable by pterostilbene formulation include actinic keratoses (AKs) and other pre-cancerous lesions.

Materials and Methods Section for UV-B Radiation Treatment

Reagents and Cell Culture

Normal human melanocytes were isolated from de-identified newborn foreskin from circumcision surgery in accordance with a protocol approved by UC Irvine's Internal Review Board. Melanocytes were isolated as previously described (Eisinger, et al., *Proc. Natl. Acad. Sci. USA* (1982) 79(6): 2018-22; and Liu, et al., *J. Invest. Dermatol.* (2009) 129(2): 422-31), and cultured in MCDB 153 media supplemented with 2% fetal bovine serum, 10 ng/ml of 12-O-tetradecanoylphorbol-13-acetate and 0.15% bovine pituitary extract. Pterostilbene was obtained from ChromaDex, Inc. (Irvine, Calif.).

UV-B Radiation Treatment of Melanocytes

UV-B irradiation was performed as previously described (Liu, F., et al., "MiTF links Erk1/2 kinase and p21 CIP1/WAF1 activation after UVC radiation in normal human melanocytes and melanoma cells," *Mol. Cancer* (2010) 9: 214). Cells were grown to about 70% confluence and media was removed completely for UV-B radiation treatment. UVB irradiation was performed in a Stratalinker UV crosslinker apparatus (Stratagene, La Jolla, Calif.) with peak wavelength at 312 nm. The UV intensity was measured by a radiometer with proper probes. The culture media was replaced immediately after radiation treatment and cells were returned to a 37° C.

incubator to recover. For chronic exposures, this process was repeated every hour for a total of five exposures. Times indicated herein always reflect time following first exposure.

Total RNA Isolation, Reverse Transcription and Real-Time PCR

Total RNA was isolated from cells using the Arum total RNA mini Kit (BioRad, Hercules, Calif.) according to the standard manufacturer's protocol. RNA was quantitated using a NanoDrop 1000 (Thermo/Fisher, Wilmington, Del.) cDNA was then made from 1.0 µg of RNA using the iScript Reverse Transcriptase Kit (BioRad) according to standard protocols. To analyze UGT mRNA expression levels in melanocytes real-time PCR was performed as previously described (Chen, G., et al., "Identification of a prevalent functional missense polymorphism in the UGT2B10 gene and its association with UGT2B10 inactivation against tobacco-specific nitrosamines," *Pharmacogenet. Genomics* (2008) 18(3): 181-91; and Dellinger, R. W., et al., "Glucuronidation of PhIP and N—OH-PhIP by UDP-glucuronosyltransferase 1A10," Carcinogenesis (2007) 28(11): 2412-8). Accordingly, pre-designed TaqMan Gene Expression Assays (Applied Biosystems, Carlsbad, Calif.) (ID's Hs00426592_m1 for UGT2B7; Hs02556282_s1 for UGT2B10; Hs03008769 g1 for UGT2B15; Hs0016857_m1 for NQO1 and Hs99999905_m1 for GAPDH) were used according to manufacturer's protocol. Real-time PCR was performed using a total volume of 20 µl containing 50 ng of cDNA using glyceraldehyde 3-phosphate dehydrogenase (GAPDH) as the normalizing 'housekeeping' gene and positive control. Real-time PCR was performed on a CFX96 Real-Time PCR machine (BioRad). Reported mRNA expression values are the average of at least 3 independent experiments with standard deviation.

The methods described above may be further understood in connection with the following Examples.

Example A

Figure 2:
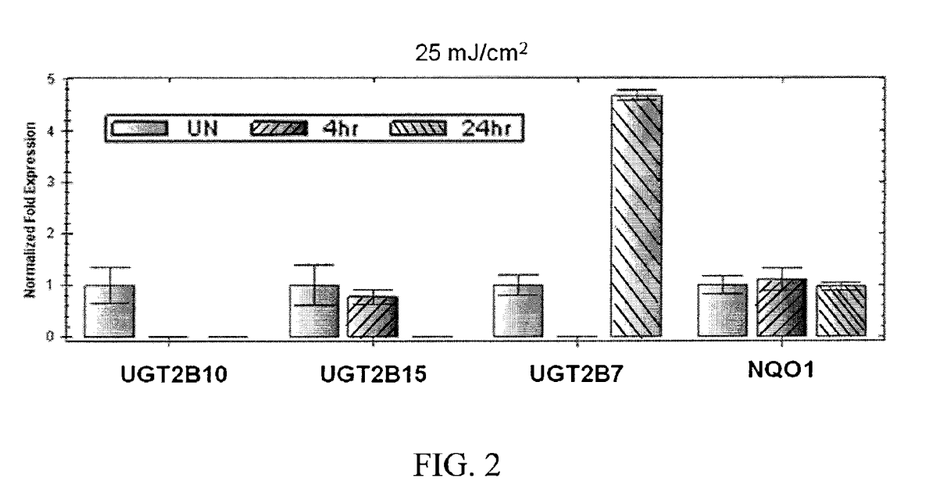
FIG. 2 depicts UV-B downregulation of UGTs in normal human melanocytes exposed to a single dose of UV-B at 25 mJ/cm$^2$. Solid bar: untreated cells; diagonally-line bars: UV-B treated cells at 4 hr and 24 hr, left to right, respectively.

Downregulation of UGT Expression in Normal Human Melanocytes Following Acute UV-B Exposure UGT2B7, UGT2B10 and UGT2B15 were found to be expressed in human melanocytes isolated from de-identified neonatal foreskins. Further, no UGT expression was observed in 4 of 5 melanoma cell lines examined. This raises the intriguing possibility that loss of UGT expression is part of melanoma etiology. To determine if UV-B could regulate UGT expression in melanocytes, once again melanocytes were isolated from de-identified neonatal foreskins and cultured. These cells were then exposed to a single dose of UV-B at 25 mJ/cm$^2$, which is approx. equivalent to a sunburn dose. Cells were subsequently collected at 0 hr, 4 hr and 24 hrs post irradiation and assayed for UGT expression using real-time PCR normalizing to GAPDH expression as described in materials and methods above. As shown in FIG. 2, expression levels of UGT2B7, UGT2B10 and UGT2B15 were all decreased in response to an acute UV-B dose. Specifically, UGT2B7 expression is undetectable 4 hrs post irradiation although its expression returns to elevated levels by 24 hours post exposure. UGT2B10 expression is lost by 4 hrs and remains undetectable 24 hours post treatment, while UGT2B15 expression levels are unchanged at 4 hrs, but undetectable by 24 hours post irradiation. NADPH dehydrogenase quinone 1 (NQO1) is used as a control since its expression did not change following UV-B exposure. This was the first demonstration that UGT expression can be regulated by UV-B exposure and is consistent with an increased risk of melanoma associated with acute UV exposure.

Example B

Figure 3:
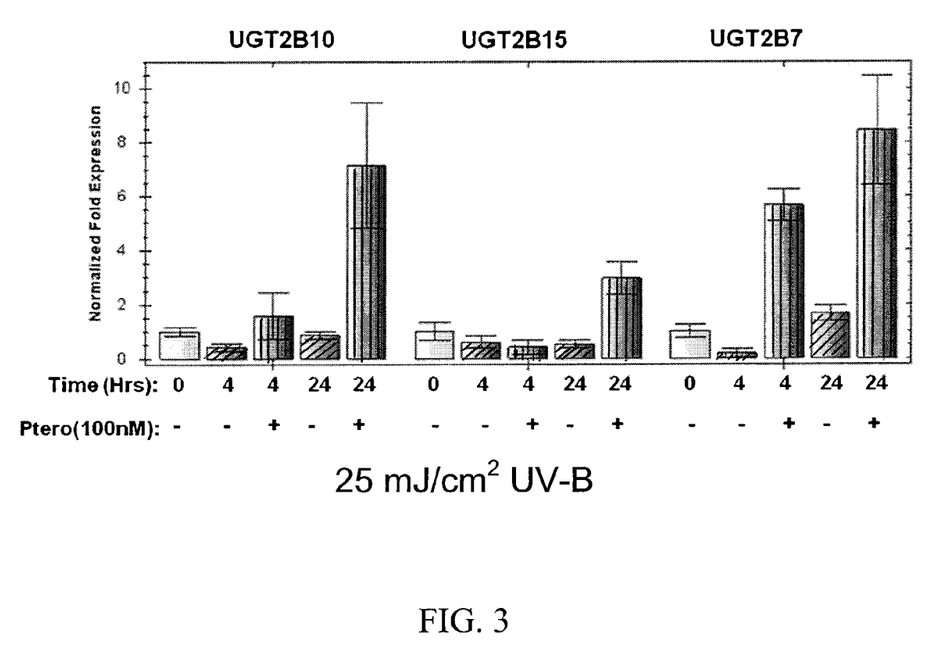
FIG. 3 depicts in one embodiment UV-B induced loss of UGT2 isoforms in normal human melanocytes, and prevention of said loss with pterostilbene (Ptero). UV-B dose: 25 mJ/cm$^2$. Solid bar: untreated cells; diagonally-line bar: UV-B treated cells; vertically-lined bar: UV-B treated and pterostilbene treated (100 nM).

Pterostilbene Treatment after UV-B-Induced Loss of UGT Expression in Human Melanocytes Here it was examined whether pterostilbene could prevent the loss of UGTs in response to acute UV-B exposure at a sunburn dose (25 mJ/cm$^2$). The Caucasian/Hispanic melanocyte cell line as described above was left untreated or treated with 100 nM pterostilbene for 1 hour. Then cells were irradiated as described above and 100 nM pterostilbene was replaced along with cell media after irradiation. As shown in FIG. 3, pterostilbene prevented loss of UGT2B7, UGT2B10 and UGT2B15 at both 4 hrs and 24 hrs post irradiation with the sole exception of UGT2B15 expression at 4 hrs. All three UGTs were found at elevated levels (up to 8-fold) 24 hrs after treatment with pterostilbene.

Thus, it has been demonstrated that the natural product pterostilbene can prevent UV-B-induced loss, or reduce the risk of loss, of UGT expression in human melanocytes. It is noted that the same procedures may be performed using human keratinocytes.

Example C

UGT Expression in Normal Human Keratinocytes

Figure 4:
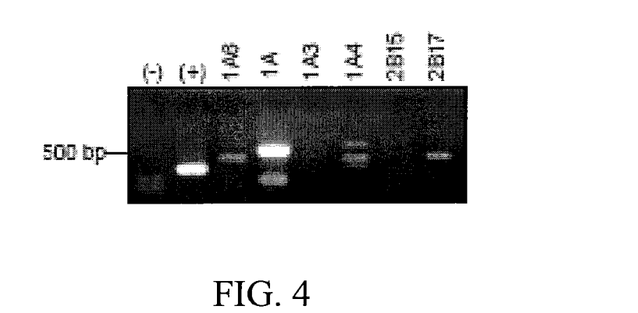
FIG. 4 depicts in another embodiment UGT mRNA expression in primary culture normal human keratinocytes by RT-PCR analysis of total mRNA for UGT isoform family members (GAPDH as positive control).

Keratinocytes are the predominant type of cell in the epidermis (about 95% of the cells in the epidermis). NMSC can arise from these cells. To ascertain if these important skin cells expressed UGTs, RT-PCR was performed. As shown in FIG. 4, UGT1A4, UGT1A6 and UGT2B17 were shown to be expressed in primary culture human keratinocytes (normal) isolated from neonatal foreskin. Bands of the expected sizes were excised and sequenced using standard methods to confirm their identities as the indicated UGT. This was the first characterization of UGT expression in human keratinocytes.

FIG. 4 shows UGT mRNA expression in primary culture human keratinocytes. RT-PCR analysis of total mRNA from human keratinocytes for the indicated UGT family members was performed. GAPDH primers were used as a positive control (+). No other UGT family member was detected.

Example D

Figure 5:
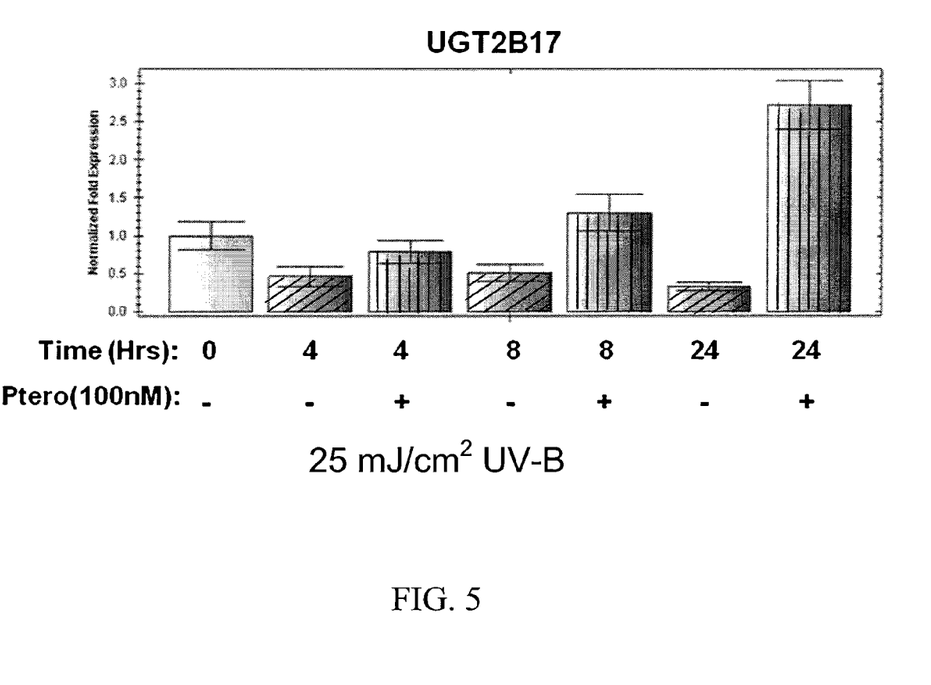
FIG. 5 depicts in another embodiment UV-B induced loss of UGT2B17 isoform in normal human keratinocytes, and prevention of said loss with pterostilbene. UV-B dose: 25 mJ/cm$^2$. Solid bar: untreated cells; diagonally-line bar: UV-B treated cells; vertically-lined bar: UV-B treated and pterostilbene treated (100 nM).

Pterostilbene Treatment after UV-B-Induced Loss of UGT2B17 Expression in Human Keratinocytes Here it was examined whether UGT2B17 expression could be regulated by UV-B radiation, and whether pterostilbene could prevent the loss. Human keratinocytes were exposed to 25 mJ/cm$^2$ UV-B radiation in the presence or absence of pterostilbene (100 nM) and collected 0 hr, 2 hr, 4 hr, 8 hr, and 24 hours post irradiation. Real-time PCR was then performed using a TaqMan assay specific for UGT2B17. As shown in FIG. 5, UGT2B17 mRNA expression is significantly downregulated in as little as 4 hours post UV-B exposure and stays low through at least 24 hours. Importantly, pterostilbene treatment as above (100 nM) abrogates UV-B-mediated UGT2B17 loss.

As shown in FIG. 5, pterostilbene prevented loss of UGT2B17 at 4 hrs, 8 hrs, and 24 hrs post irradiation. Relative mRNA expression of UGT2B17 is shown normalized to the GAPDH with 0 hrs arbitrarily set to 1.0.

Thus, it has been demonstrated that the natural product pterostilbene can prevent UV-B-induced loss, or reduce the risk of loss, of UGT expression in human keratinocytes.

Example E

Inhibition of 12-LOX Expression in Human Melanoma Cells by Pterostilbene (Ptero)

Figure 6:
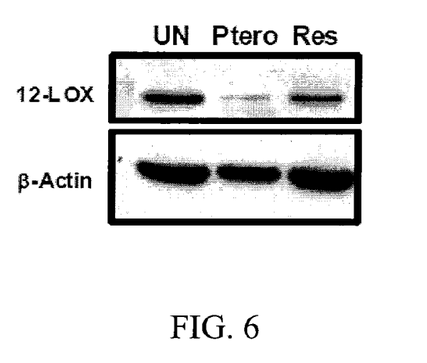
FIG. 6 depicts in another embodiment 12-LOX expression by Western blot after treatment of SKmel28 human melanoma cells with pterostilbene (Ptero) or resveratrol (Res) at 50 μM (B-actin as loading control).

As shown in FIG. 6, pterostilbene (50 μM) substantially blocked 12-LOX activity in vitro, testing by known methods. Western blot of 12-LOX from SKmel28 human melanoma cells left untreated (UN) or treated with 50 μM of pterostilbene (Ptero) or resveratrol (Res) as indicated. B-actin was used as a loading control. It was observed that pterostilbene inhibited 12-LOX expression better than resveratrol in vitro.

Example F

12-HETE Activity in Normal Skin and Human AKs

Figure 7:
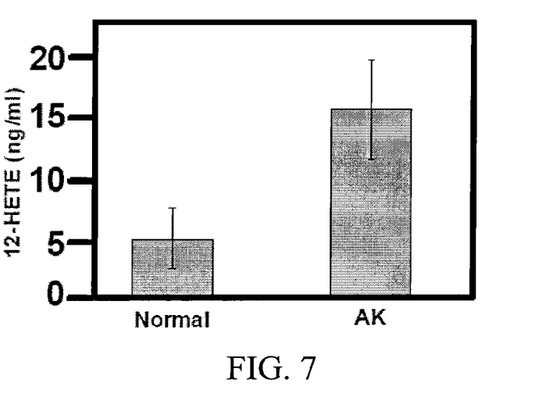
FIG. 7 depicts measured levels of 12-HETE in normal skin and AKs from the same human patient (n=6).

Using standard methods, the lipid fraction was extracted from 3 mm skin punch biopsies of normal skin or AK from the same patient and analyzed by LC/MS/MS standard method to determine 12-HETE concentration (n=6 patients, normal and AK sample taken from each). As shown in FIG. 7, 12-HETE levels were 3-fold higher in actinic keratosis (AK) as compared to normal skin from the same individual.

This was novel data as 12-HETE levels in AKs have not previously been reported. Also, this data is necessary in order to use 12-HETE as a clinical endpoint in the clinical trial as described. This data correlates well with mouse studies showing deregulation of 12-HETE (Krieg, P., et al., "12-Lipoxygenase isoenzymes in mouse skin tumor development," *Mol. Carcinog.* (1995) 14(2): 118-129).

Since 12-LOX produces 12-HETE, it is expected that reduction of 12-LOX expression by pterostilbene in proliferating or pre-cancerous cells will prevent or reduce 12-HETE formation and/or pterostilbene will be effective to restore 12-HETE to normal levels in damaged skin (both by inhibiting 12-LOX and by upregulating UGTs). It is further expected that treatment of proliferating or pre-cancerous cells will result in regression or reversion of AKs (and optionally NMSCs).

Example 1

In accordance with one embodiment, a patient (or each member of a patient cohort) is treated with a daily dosage of 100 mg pterostilbene formulated in an acceptable nutraceutical carrier, administered orally as follows. 100 mg pterostilbene and 150 mg microcrystalline cellulose are combined in a vegetable capsule. After identifying AKs (and optionally NMSCs) from a skin test area on the forearm of the patient (8 cm$^2$), and mapping, photographing, imaging, and taking biopsies of the lesions, a clinical study is carried out as detailed above. After 12 weeks of study monitoring, it is expected that an individual human subject will exhibit regression of AKs identified in the skin test area.

Example 1A

In accordance with an embodiment, a patient (or each member of a patient cohort) is treated with a daily dosage of 100 mg pterostilbene formulated in an acceptable nutraceutical carrier, administered orally. After identifying AKs (and optionally NMSCs) from a skin test area on the forearm of the patient (8 cm$^2$), and mapping, photographing, imaging, and taking biopsies of the lesions, a clinical study is carried out as detailed above. It is expected that in the course of the study over 12 weeks, UGT expression in the pre-cancerous tissue samples as a function of mRNA or protein will be significantly increased.

Example 1B

In accordance with one embodiment, a patient (or each member of a patient cohort) is treated with a daily dosage of 100 mg pterostilbene formulated in an acceptable nutraceutical carrier, administered orally. After identifying AKs (and optionally NMSCs) from a skin test area on the forearm of the patient (8 cm$^2$), and mapping, photographing, imaging, and taking biopsies of the lesions, a clinical study is carried out as detailed above. It is expected that in the course of the study over 12 weeks, 12-HETE levels in the pre-cancerous tissue samples will be significantly reduced.

Example 2

In accordance with one embodiment, a patient (or each member of a patient cohort) is treated with a daily dosage of 100 mg pterostilbene formulated in an acceptable nutraceutical carrier, administered orally as follows. 100 mg pterostilbene and 150 mg microcrystalline cellulose are combined in a vegetable capsule. After identifying AKs (and optionally NMSCs) from a skin test area on the forearm of the patient (8 cm$^2$), and mapping, photographing, imaging, and taking biopsies of the lesions, a clinical study is carried out as detailed above. After 12 weeks of study monitoring, it is expected that the treatment will prevent progression of pre-cancerous AKs into NMSC identified in the skin test area, and/or suppress formation of new NMSC in the individual human subject.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of treating an individual for actinic keratosis or dysplastic nevi, comprising administering to the individual in need of such treatment a therapeutically effective amount of the compound pterostilbene wherein UDP-glucuronosyltransferase (UGT) activity is increased.

2. The method of claim 1, wherein the individual is a human.

3. The method of claim 2, wherein the pterostilbene compound is provided in a composition comprising a pharmaceutically or nutraceutically acceptable carrier.

4. The method of claim 3, wherein the therapeutically effective amount of pterostilbene for a total dose is in a range of about 0.1% by weight to about 10% by weight based on the total weight of the composition.

5. The method of claim 3, wherein the therapeutically effective amount of pterostilbene for a total dose is in a range of about 0.1% by weight to about 0.5% by weight based on the total weight of the composition.

6. The method of claim 3, wherein the therapeutically effective amount of pterostilbene for a total daily dose is in a range of about 5 mg to about 1000 mg.

7. The method of claim 3, wherein the therapeutically effective amount of pterostilbene for a total daily dose is in a range of about 50 mg to about 250 mg.

8. The method of claim 6, wherein the route of administration of the compound is selected from the group consisting of oral, topical, intradermal, transdermal, and subcutaneous.

9. The method of claim 1, further wherein 12-HETE levels are reduced in the actinic keratosis or dysplastic nevi.

10. A method of inhibiting UV-induced loss of UDP-glucuronosyltransferase (UGT) activity in an individual afflicted with actinic keratosis or dysplastic nevi, comprising administering to the individual in need of such treatment a therapeutically effective amount of the compound pterostilbene wherein UDP-glucuronosyltransferase (UGT) activity is increased.

11. The method of claim 10, wherein the individual is a human.

12. The method of claim 11, wherein the pterostilbene compound is provided in a composition comprising a pharmaceutically or nutraceutically acceptable carrier.

13. The method of claim 12, wherein the therapeutically effective amount of pterostilbene for a total dose is in a range of about 0.1% by weight to about 10% by weight based on the total weight of the composition.

14. The method of claim 12, wherein the therapeutically effective amount of pterostilbene for a total dose is in a range of about 0.1% by weight to about 0.5% by weight based on the total weight of the composition.

15. The method of claim 12, wherein the therapeutically effective amount of pterostilbene for a total daily dose is in a range of about 5 mg to about 1000 mg.

16. The method of claim 12, wherein the therapeutically effective amount of pterostilbene for a total daily dose is in a range of about 50 mg to about 250 mg.

17. The method of claim 15, wherein the route of administration of the compound is selected from the group consisting of oral, topical, intradermal, transdermal, and subcutaneous.

18. The method of claim 10, further wherein 12-HETE levels are reduced in the actinic keratosis or dysplastic nevi.

\* \* \* \* \*